(12) United States Patent
Lee et al.

(10) Patent No.: US 11,600,014 B2
(45) Date of Patent: Mar. 7, 2023

(54) POSE ESTIMATION METHOD OF BENDABLE INTERVENTIONAL MEDICAL DEVICE USING SINGLE-VIEW X-RAY IMAGE

(71) Applicant: KOREA INSTITUTE OF SCIENCE AND TECHNOLOGY, Seoul (KR)

(72) Inventors: Deuk Hee Lee, Seoul (KR); Sung Hwan Lim, Seoul (KR); Jun Hyoung Ha, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 309 days.

(21) Appl. No.: 17/024,293

(22) Filed: Sep. 17, 2020

(65) Prior Publication Data
US 2021/0334999 A1    Oct. 28, 2021

(30) Foreign Application Priority Data
Apr. 22, 2020    (KR) .................. 10-2020-0048606

(51) Int. Cl.
G06T 7/73     (2017.01)
G06T 7/60     (2017.01)
A61M 25/01    (2006.01)

(52) U.S. Cl.
CPC .................. G06T 7/73 (2017.01); G06T 7/60 (2013.01); A61M 25/0108 (2013.01);
(Continued)

(58) Field of Classification Search
CPC ... G06T 7/73; G06T 7/60; G06T 2207/30048; G06T 2207/30204; G06T 2207/30021; G06T 2207/10116; A61M 25/0108
See application file for complete search history.

(56) References Cited

U.S. PATENT DOCUMENTS 8,682,062 B2    3/2014  Kim et al.
2012/0082342 A1*  4/2012  Kim ...................... G06T 7/74
                                        382/103
(Continued)

FOREIGN PATENT DOCUMENTS

KR    101188715 B1    10/2012
KR    101892631 B1    8/2018
(Continued)

OTHER PUBLICATIONS

Chang, et al. ("Constrained least squares optimization for robust estimation of center of rotation," Elsevier, May 7, 2006, CMU, pp. 1-12).*
(Continued)

*Primary Examiner* — Shefali D Goradia
(74) *Attorney, Agent, or Firm* — Rabin & Berdo, P.C.

(57) ABSTRACT

The present invention relates to a pose estimation method of an interventional medical device using a single-view X-ray image which is captured using a bendable interventional medical device equipped with a plurality of radiopaque markers and using an X-ray source. The pose estimation method includes an operation (a) of defining a circle assuming that the interventional medical device is bent at a constant curvature, an operation (b) of extracting a position value of the marker from an X-ray image obtained by the X-ray source projecting X-rays onto the markers, and an operation (c) of setting a projection plane and estimating a shape of the circle using a position value of the marker extracted from a projected image obtained by perspective-projecting the circle onto the projection plane and using the position value of the marker extracted from the X-ray image.

12 Claims, 12 Drawing Sheets

(52) U.S. Cl.
CPC .............. *G06T 2207/10116* (2013.01); *G06T 2207/30021* (2013.01); *G06T 2207/30048* (2013.01); *G06T 2207/30204* (2013.01)

(56) References Cited

U.S. PATENT DOCUMENTS

| | | | |
|---|---|---|---|
| 2013/0243153 A1* | 9/2013 | Sra | A61B 6/485 378/62 |
| 2018/0249973 A1* | 9/2018 | Lee | A61B 90/361 |

FOREIGN PATENT DOCUMENTS

| | | | | |
|---|---|---|---|---|
| WO | WO-2017139591 A1 * | 8/2017 | ............. | A61B 34/10 |
| WO | WO-2017139621 A1 * | 8/2017 | ............. | A61B 34/20 |

OTHER PUBLICATIONS

C. Doignon et al., "A degenerate conic-based method for a direct filling and 3-D pose of cylinders with a single perspective view," in Proceedings 2007 IEEE International Conference on Robotics and Automation. IEEE, Apr. 10-14, 2007, pp. 4220-4225.

C. Doignon et al., "The role of insertion points in the detection and positioning of instruments in laparoscopy for robotic tasks," in International Conference on Medical Image Computing and Computer-Assisted Intervention. Springer, 2006, pp. 527-534.

C. Gouveia et al., "Temperature-independent curvature sensor using FBG cladding modes based on a core misaligned splice," IEEE Photonics Technology Letters, vol. 23, No. 12, pp. 804-806, Jun. 2011.

J. Leven et al., "DaVinci canvas: a telerobotic surgical system with integrated, robotassisted, laparoscopic ultrasound capability," in International Conference on Medical Image Computing and Computer-Assisted Intervention. Springer, 2005, pp. 811-818.

R. M. Haralick et al., "Analysis and solutions of the three points perspective pose estimation problem." In CVPR, vol. 91, Jun. 1991, pp. 592-598.

S. C. Ryu et al., "FBG-based shape sensing tubes for continuum robots," in 2014 IEEE International Conference on Robotics and Automation (ICRA). IEEE, May 2014, pp. 3531-3537.

S. Hwang et al., "3D pose estimation of catheter band Markers based on single-plane fluoroscopy," in 2018 15th International Conference on Ubiquitous Robots (UR). IEEE, Jun. 27-30, 2018, pp. 723-728.

S. Shin et al., "A single camera tracking system for 3D position, Grasper angle, and rolling angle of laparoscopic instruments," International Journal of Precision Engineering and Manufacturing, vol. 15, No. 10, pp. 2155-2160, Oct. 2014.

Z. Lunwei et al., "FBG sensor devices for spatial shape detection of intelligent colonoscope," in IEEE International Conference on Robotics and Automation, 2004. Proceedings. ICRA'04. 2004, vol. 1. IEEE, Apr. 2004, pp. 835-840.

* cited by examiner s300a

FIG. 10C
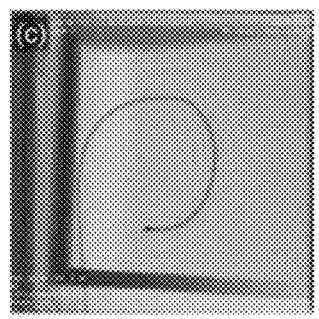
FIG. 10D
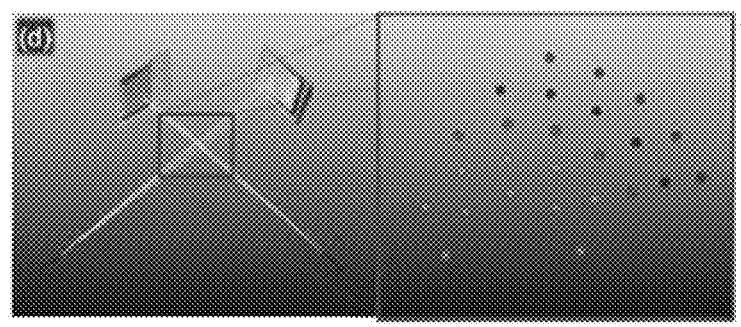
FIG. 11
| | MARKER POSITION ERROR (mm) | | | | | CURVATURE RADIUS ERROR (mm) | PLANE NORMAL VECTOR ERROR (°) |
|---|---|---|---|---|---|---|---|
| | 1 | 2 | 3 | 4 | 5 | | |
| SLOT #1 | 3.84 | 4.20 | 4.33 | 4.41 | 4.78 | 0.08 | 0.77 |
| SLOT #2 | 7.58 | 7.80 | 7.76 | 7.81 | 7.86 | 0.53 | 0.52 |
| SLOT #3 | 2.42 | 2.51 | 2.18 | 2.03 | 1.38 | 1.44 | 1.14 |
| SLOT #4 | 1.34 | 1.30 | 1.17 | 1.08 | 0.98 | 0.66 | 0.42 |
| SLOT #5 | 2.18 | 2.19 | 1.74 | 1.74 | 1.84 | 0.23 | 1.02 |

(a)

(b)

POSE ESTIMATION METHOD OF BENDABLE INTERVENTIONAL MEDICAL DEVICE USING SINGLE-VIEW X-RAY IMAGE

CROSS-REFERENCE TO RELATED APPLICATION

This application claims priority to and the benefit of Korean Patent Application No. 2020-0048606, filed on Apr. 22, 2020, the disclosure of which is incorporated herein by reference in its entirety.

BACKGROUND

1. Field of the Invention

The present invention relates to a pose estimation method of a bendable interventional medical device using a single-view X-ray image.

2. Discussion of Related Art

Bendable interventional medical devices including flexible catheters and flexible endoscopes are widely used in numerous clinical medical treatments and/or surgeries, such as cardiac catheter ablation, retrograde intra-renal surgery using flexible ureteroscopy, percutaneous coronary intervention, epidural epiduroscopy, and the like.

The most important task required in such medical treatment and/or surgery is accurately checking a three-dimensional (3D) position and pose of a bendable device to reach a target point rapidly and accurately. To this end, single-view X-ray devices are generally used. An X-ray image is obtained when it is necessary for a clinician to check a current position of an interventional device inserted into a patient. Next, the clinician estimates a 3D position and pose of the interventional medical device on the basis of two-dimensional (2D) X-ray image information and medical experience.

The X-ray image may be used to immediately check the current position of the interventional medical device, but the current position of the interventional medical device is limited to a position and pose in a 2D space. The estimation of the 3D position and pose of the interventional medical device using the 2D X-ray image is a difficult process for a less experienced clinician to perform rapidly. Further, when the 3D position and pose of the device are incorrectly determined, a medical treatment and/or surgery time may be increased and X-ray photographing should be done multiple times, and thus patients and medical staffs may be excessively exposed to radiation.

Several methods for position and pose tracking of 3D surgical devices based on 2D images have been reported by other researchers.

In Non-Patent Document 1, a solution to the problem of position and pose estimation using points is proposed. The problem of position and pose estimation using three points lies in using a 2D projected image of the given three points to determine 3D positions and poses of the three points.

In Patent Documents 1 and 2 and Non-Patent Document 2, methods of estimating a 3D position of an end of a catheter from a single X-ray image using the above idea are proposed.

In Non-Patent Documents 3 and 4, methods of estimating a 3D position and pose of a linear surgical tool from a 2D single projected image are proposed.

In Non-Patent Document 5, a system that includes a method of estimating a 3D position, pose, and an axial rotation angle of a laparoscopic ultrasound probe integrated in a "da Vinci" surgical robot is proposed.

In Patent Documents 3 and 4 and Non-Patent Document 6, similar techniques are proposed in which a 3D position, grasper angle, and axial rotation angle of a laparoscopic device using a single camera are estimated.

However, all of the above studies aim to estimate the 3D position and pose of the linear surgical device. The solution disclosed in Non-Patent Document 1 and the like may be used for three points that are not collinear, but relative positions of the three points should be known in advance and should not be changed. On the other hand, in the case of a bendable interventional medical device, a shape of the device is not fixed and is changed continuously during treatment and/or surgery. Therefore, the above techniques cannot be directly applied to estimate a 3D position and pose of a bendable interventional medical device such as a flexible catheter and a flexible endoscope.

Referring to Non-Patent Documents 7 to 9, several researchers use fiber Bragg grating (FBG) sensors to estimate a 3D pose and curvature of a bendable interventional medical device. The FBG sensor provides information about a 3D position, pose and curvature of the bendable interventional medical device in real time, but the FBG sensor has several problems, such as high manufacturing cost and high level of difficulty, a need for additional devices for signal processing, and a temperature-dependent characteristic.

A function in which the 3D position, pose, and curvature of the bendable interventional medical device are checked rapidly during medical treatment is critical for clinicians to make better decisions during surgery. Ultimately, the better decisions made by the clinicians can lead to rapid performance of the medical treatment and/or surgery and to minimization of radiation exposure of patients and/or medical staffs.

DOCUMENT OF RELATED ART

Patent Document (Patent Document 1) Korean Patent No. 10-1892631
(Patent Document 2) U.S. patent application Ser. No. 15/631,032, Application Date: Jun. 23, 2017
(Patent Document 3) Korean Patent No. 10-1188715
(Patent Document 4) U.S. Pat. No. 8,682,062, Registration Date: Mar. 25, 2014

Non-Patent Document (Non-Patent Document 1) "R. M. Haralick, C.-n. Lee, K. Ottenburg, and M. N¨olle, "Analysis and solutions of the three points perspective pose estimation problem." In CVPR, vol. 91, 1991, pp. 592-598"
(Non-Patent Document 2) "S. Hwang and D. Lee, "3d pose estimation of catheter band markers based on single-plane fluoroscopy," in 201815th International Conference on Ubiquitous Robots (UR). IEEE, 2018, pp. 723-728"
(Non-Patent Document 3) "C. Doignon, F. Nageotte, and M. de Mathelin, "The role of insertion points in the detection and positioning of instruments in laparoscopy for robotic tasks," in International Conference on Medical Image Computing and Computer-Assisted Intervention. Springer, 2006, pp. 527-534"
(Non-Patent Document 4) "C. Doignon and M. de Mathelin, "A degenerate conic-based method for a direct fitting and 3-d pose of cylinders with a single perspective view," in Proceedings 2007 IEEE International Conference on Robotics and Automation. IEEE, 2007, pp. 4220-4225"

(Non-Patent Document 5) "J. Leven, D. Burschka, R. Kumar, G. Zhang, S. Blumenkranz, X. D. Dai, M. Awad, G. D. Hager, M. Marohn, M. Choti et al., "Davinci canvas: a telerobotic surgical system with integrated, robot-assisted, laparoscopic ultrasound capability," in International Conference on Medical Image Computing and Computer-Assisted Intervention. Springer, 2005, pp. 811-818"

(Non-Patent Document 6) "S. Shin, Y. Kim, H. Cho, D. Lee, S. Park, G J. Kim, and L. Kim, "A single camera tracking system for 3d position, grasper angle, and rolling angle of laparoscopic instruments," International journal of precision engineering and manufacturing, vol. 15, no. 10, pp. 2155-2160, 2014"

(Non-Patent Document 7) "Z. Lunwei, Q. Jinwu, S. Linyong, and Z. Yanan, "Fbg sensor devices for spatial shape detection of intelligent colonoscope," in IEEE International Conference on Robotics and Automation, 2004. Proceedings. ICRA'04. 2004, vol. 1. IEEE, 2004, pp. 834-840"

(Non-Patent Document 8) "C. Gouveia, P. Jorge, J. Baptista, and O. Frazao, "Temperature independent curvature sensor using fbg cladding modes based on a core misaligned splice," IEEE Photonics Technology Letters, vol. 23, no. 12, pp. 804-806, 2011"

(Non-Patent Document 9) "S. C. Ryu and P. E. Dupont, "Fbg-based shape sensing tubes for continuum robots," in 2014 IEEE International Conference on Robotics and Automation (ICRA). IEEE, 2014, pp. 3531-3537"

SUMMARY OF THE INVENTION

The present invention is directed to providing a pose estimation method of an interventional medical device, in which a three-dimensional (3D) position and pose of a bendable interventional medical device are estimated by using only one X-ray image.

According to an aspect of the present invention, there is provided a pose estimation method of an interventional medical device using a single-view X-ray image which is captured using a bendable interventional medical device equipped with a plurality of radiopaque markers and using an X-ray source. The pose estimation method includes an operation (a) of defining a circle assuming that the interventional medical device is bent at a constant curvature, an operation (b) of extracting a position value of the marker from an X-ray image obtained by the X-ray source projecting X-rays onto the markers, and an operation (c) of setting a projection plane and estimating a shape of the circle using a position value of the marker extracted from a projected image obtained by perspective-projecting the circle onto the projection plane and using the position value of the marker extracted from the X-ray image.

In the operation (c), when there are four radiopaque markers, the position value of the marker extracted from the projected image may have parameters of a center position, a radius, and a rotation matrix of a circle.

The operation (c) may include an operation of calculating values of the parameters of the center position, the radius, and the rotation matrix of the circle by applying least squares minimization.

In the operation (c), when there are five radiopaque markers, the position value of the marker extracted from the projected image may have parameters of a center position, a radius, and a plane normal vector of the circle.

The operation (c) may include an operation (c-1) of defining the position value of the marker extracted from the projected image using a parameter matrix and estimating each of matrix components corresponding to the position value of the marker in the parameter matrix using a preset criterion, and an operation (c-2) of calculating normalized circle parameters including a normalized radius, a normalized center position, and the plane normal vector from the parameter matrix.

The pose estimation method may further include an operation (d) of estimating the position of the marker from the normalized circle parameters after the operation (c).

In the operation (c-1), the parameter matrix may be a symmetric 3×3 matrix with six independent components.

In the operation (c-1), the parameter matrix may be estimated by applying least squares minimization.

The pose estimation method may further include, after the operation (c-1) and before the operation (c-2), an operation of adjusting a size of the parameter matrix such that the second largest eigenvalue of the parameter matrix is 1.

The operation (c-2) may include an operation of calculating an eigenvector and a plurality of eigenvalues of the parameter matrix using a preset eigenvalue decomposition criteria and calculating a normalized radius.

In the operation (c-2), the normalized circle parameters may further include the normalized center position and the plane normal vector. The operation (c-2) may further include an operation of calculating an eigenvector matrix using the fact that a trace of the parameter matrix is the sum of the eigenvalues of the parameter matrix, and an operation of identifying the eigenvalues of the parameter matrix using the fact that the eigenvector of the parameter matrix is orthogonal to an eigenvector of a symmetric matrix and calculating the normalized center position and the plane normal vector by inverting the eigenvector matrix.

The operation (d) may include an operation of calculating a position of the marker on the normalized circle, and an operation of scaling sizes of the normalized circle and the position of the marker such that an actual marker distance matches a marker distance on the projected image.

The operation of calculating the position of the marker may include an operation of calculating an intersection between a plane of the normalized circle and a line following a vector of the marker positions on the projected image and an operation of calculating an estimate by projecting the intersection onto the normalized circle.

The operation of scaling the normalized circle and the position of the marker may include an operation of calculating a scale by applying least squares minimization using a length between the markers along the normalized circle and using an actual length between the markers and an operation of estimating the position of the marker according to the scale.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIGS. 10A to 10D illustrate 3D reconstruction of positions of band markers, wherein FIG. 10A is a view illustrating an X-ray image #1, FIG. 10B is a view illustrating positions of band markers, which are reconstructed by the method according to the embodiment of the present invention, FIG. 10C is a view illustrating an X-ray image #2, and FIG. 10D is a view illustrating positions of band markers which are reconstructed by a stereo triangulation method;

FIG. 11 is a table showing errors in marker position, radius of curvature, and plane normal vector;

FIGS. 12A and 12B illustrate views illustrating comparison of estimated results and measured data, wherein FIG. 12A is a view illustrating the best estimate and FIG. 12B is a view illustrating the worst estimate.

DETAILED DESCRIPTION OF EXEMPLARY EMBODIMENTS

Hereinafter, exemplary embodiments of the present invention will be described in detail with reference to the accompanying drawings. In detailed descriptions of the present invention, it is clear to those skilled in the art but when it is determined that detailed descriptions of related well-known functions unnecessarily obscure the gist of the present invention, detailed descriptions thereof will be omitted.

Figure 1:
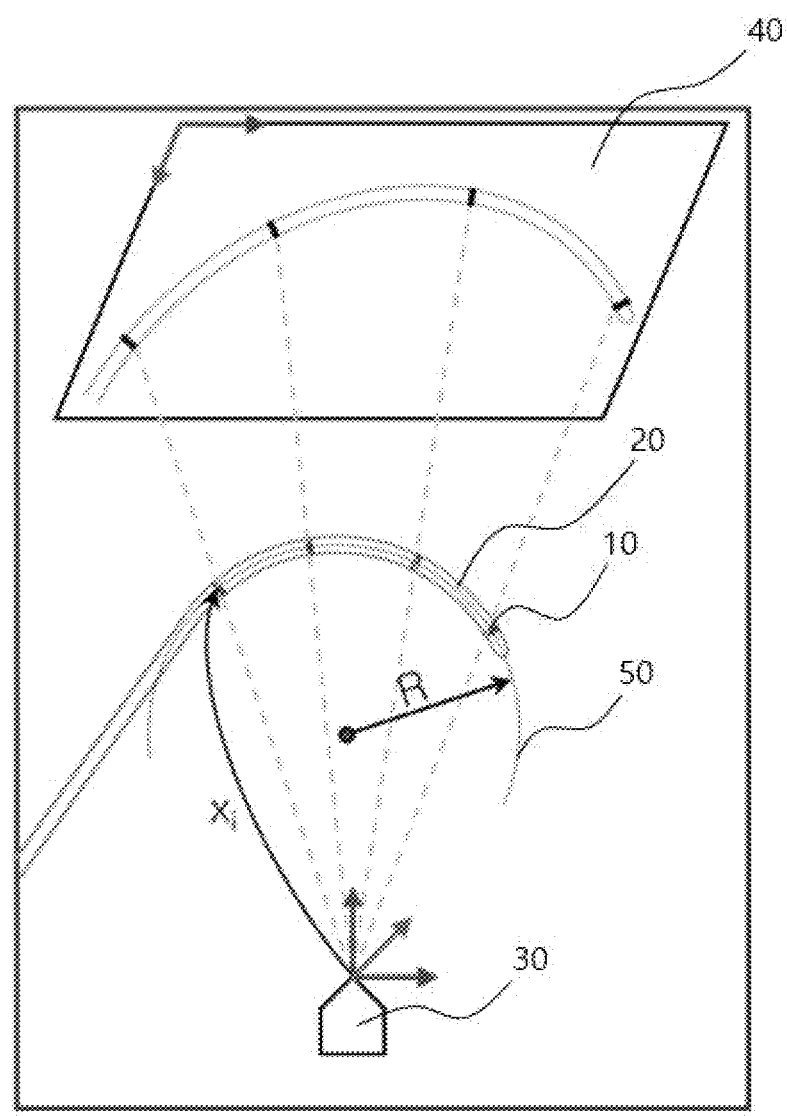
FIG. 1 is a schematic view illustrating a state in which, in order to apply a pose estimation method of an interventional medical device using a single-view X-ray image according to an embodiment of the present invention, markers are photographed using a bendable interventional medical device equipped with radiopaque markers and using an X-ray source.
Figure 2:
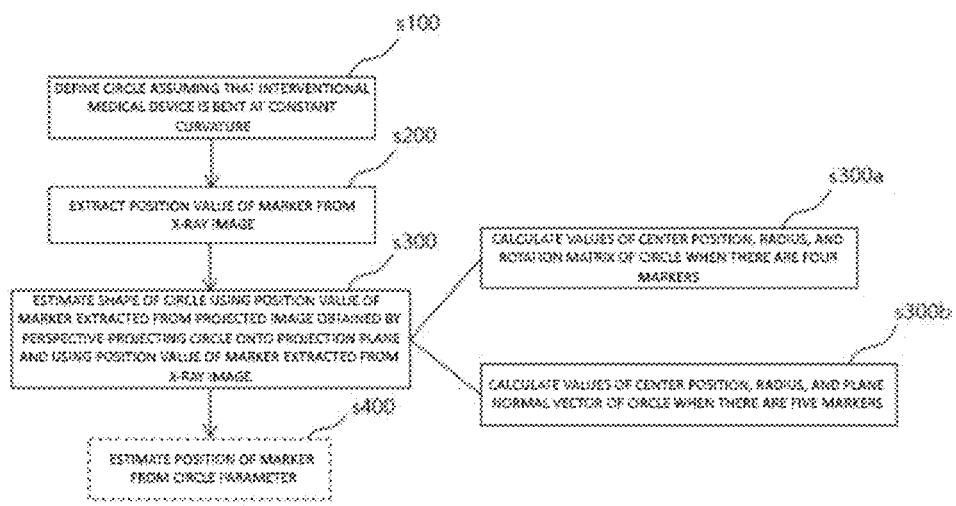
FIG. 2 is a flowchart illustrating operations of a pose estimation method of a bendable interventional medical device using a single-view X-ray image according to the embodiment of the present invention.

FIG. 1 is a schematic view illustrating a state in which, in order to apply a pose estimation method of an interventional medical device using a single-view X-ray image according to an embodiment of the present invention, markers are photographed using a bendable interventional medical device equipped with radiopaque markers and using an X-ray source. FIG. 2 is a flowchart illustrating operations of the pose estimation method of the interventional medical device according to the embodiment of the present invention.

Referring to FIG. 1, the pose estimation method of the interventional medical device according to the present invention may be used to estimate a three-dimensional (3D) pose and curvature of a bendable interventional medical device 20 equipped with a plurality of radiopaque markers 10, and each operation of the pose estimation method may be performed by a computing device such as a processor. An X-ray source 30 irradiates the interventional medical device 20 with X-rays, and the irradiated X-rays pass through the interventional medical device 20 so that an X-ray image of the interventional medical device 20 is generated on an X-ray film 40. Since the plurality of radiopaque markers 10 are mounted in the interventional medical device 20, X-ray images of the markers 10 are included in the generated X-ray image.

The pose estimation method of the interventional medical device according to the embodiment of the present invention may be applied to a bendable interventional medical device equipped with radiopaque markers. In the case in which it is assumed that the interventional medical device is bent at a constant curvature, for example, when four or more markers are mounted in the interventional medical device, a curvature and 3D pose of the interventional medical device may be measured simultaneously.

Referring to FIG. 2 further, the pose estimation method of the interventional medical device according to the present invention includes an operation s100 of defining a circle 50 assuming that the interventional medical device 20 is bent at a constant curvature, an operation s200 of extracting a position value of the marker 10 from an X-ray image obtained by the X-ray source 30 projecting X-rays onto the markers 10, and an operation s300 of setting a projection plane and estimating a shape of the circle 50 using a position value of the marker 10 extracted from a projected image obtained by perspective-projecting the circle 50 onto the projection plane and using the position value of the marker 10 extracted from the X-ray image. The operation s300 of estimating the shape of the circle 50 may include an operation s300a of estimating the shape of the circle 50 when there are four markers, and an operation s300b of estimating the shape of the circle 50 when there are five markers.

The pose estimation method may further include an operation s400 of estimating a position of the marker from parameters of the circle after the operation s300 of estimating the shape of the circle 50.

According to the embodiment, when there are four markers 10, a pose and curvature of the interventional medical device may be estimated by using a center position, a radius, and a rotation matrix of the circle 50 as parameters. Further, when there are five markers 10, a pose and curvature of the interventional medical device may be estimated by using a center position, a radius, and a plane normal vector of the circle 50 as parameters.

Hereinafter, an example in which there are four markers 10 will be described as follows.

When the interventional medical device is bent at a constant curvature, a central line of the interventional medical device is a circular arc. When R>0, a circle is defined such that $R \in \mathbb{R}$, $X_0 \in \mathbb{R}^3$, and $Y \in \mathbb{R}^{3 \times 3}$ represent a radius, a center position, and a rotation matrix of the circle, respectively (s100). In this case, a rotation matrix Y represents a coordinate axis attached to a center of the circle. A pose and a curvature of the interventional medical device may be determined by determining R, $X_0$, and Y. Since intrinsic parameters of the rotation matrix are three parameters representing x, y, and z-axis rotation, a total number of unknowns is seven.

The position values of the markers are extracted from the X-ray image obtained by the X-ray source projecting the X-rays onto the markers (s200). Since one marker is displayed in 2D coordinates on the X-ray image plane, two measurements are provided. Since there are seven or more measurements only when there are at least four markers, seven unknowns may be specified.

Figure 3:
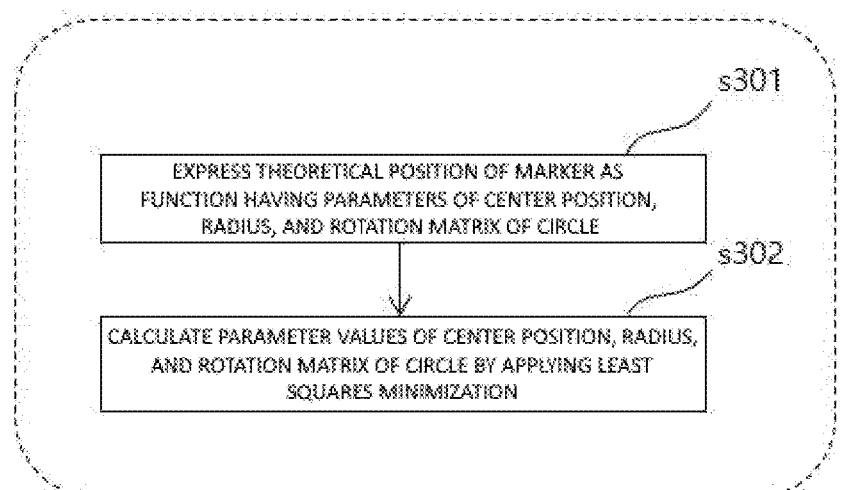
FIG. 3 is a flowchart illustrating operations of calculating parameters of a center position, a radius, and a rotation matrix of a circle when there are four markers in FIG. 2.

FIG. 3 is a flowchart illustrating operations of calculating parameters of a center position, a radius, and a rotation matrix of a circle when there are four markers in FIG. 2.

Referring to FIG. 3, the projection plane may be set, and values of the center position, the radius, and the rotation matrix of the circle may be calculated by using the position values of the markers in the projected image obtained by perspective-projecting the circle onto the projection plane and by using the position values of the markers in the X-ray image (s300a). The specific calculation method is as follows.

When the interventional medical device, to which four or more markers are attached, is photographed using X-rays, a 2D position value of an $i^{th}$ marker measured on the X-ray image is defined as $u \in \mathbb{R}^2$. When R, $X_0$, and Y are given, a theoretical 3D position of each marker may be obtained, and a theoretical 2D position value of each marker may be obtained by perspective-projecting the theoretical 3D position onto the X-ray projection plane. When the theoretical 2D coordinate value obtained in this way is defined as $w \in \mathbb{R}^2$, $w_i$ is a function of R, $X_0$, and Y and thus may be expressed as follows (s301).

$$w_i = w_i(R, X_0, Y)$$

The values of the center position ($X_0$), the radius (R), and the rotation matrix (Y) of the circle may be calculated by applying the following least squares minimization (s302).

$$(R, X_0, Y) = \arg\min_{R, X_0, Y} \|u_i - w_i(R, X_0, Y)\|^2$$

The above minimization problem may be solved by applying a nonlinear minimization algorithm. An initial value at the time of nonlinear minimization may be input arbitrarily, or when there is prior knowledge of the pose of the interventional medical device, the initial value may be determined using the prior knowledge. When the number of attached markers is five or more, an appropriate initial value may be analytically determined and contents thereof will be described below.

Hereinafter, an example in which there are five markers 10 will be described as follows.

When the interventional medical device is bent at a constant curvature, a central line of the interventional medical device is a circular arc. A circle including the central line of the interventional medical device is considered. When R>0 and $\|n\|=1$, a circle is defined so that $R \in \mathbb{R}$, $X_0 \in \mathbb{R}^3$, and $Y \in \mathbb{R}^{3 \times 3}$ represent a radius, a center position, and a rotation matrix of the circle, respectively (s100). For convenience of formulation, a normalized circle, in which a normalized center position ($x_0 \in \mathbb{R}^3$) and a normalized radius ($r \in \mathbb{R}$) are given as follows, may be defined.

$$x_0 = X_0/d, \ r = R/d \quad \text{(Equation 1)}$$

Here, d is defined by $d = n^T X_0$.

The projection plane and the perspective projection of the circle may be defined as follows.

It is assumed that perspective projection has a perspective origin of (0, 0, 0) and a projection plane of z=1. The perspective projection of the circle is invariant to normalization. The perspective projection of the circle is a quadratic function that may be derived after the following algebraic manipulation.

$$p^T Q p = 0 \quad \text{(Equation 2)}$$

Here, Q and p are given as follows.

$$Q = I - (x_0 n^T + n x_0^T) - (\|x^0\|^2 - r^2) n n^T \quad \text{(Equation 3)}$$

$$p = [x \ y \ 1]^T \quad \text{(Equation 4)}$$

Here, p denotes an arbitrary point of a projected curve.

Using Equation 3, a non-iterative method, in which a radius, a center position, and a plane normal vector of a circle, and a position of the marker are estimated when given a projected image, will be described. The method to be described includes the following operations.

1. Estimation of parameter matrix Q from projected image
2. Calculation of normalized circle parameters ($x_0$, r, n) from parameter matrix Q
3. Calculation of ($X_0$, R) and position of marker in circle FIG. 4 is a flowchart illustrating operations of calculating normalized circle parameters including a center position, a radius, and a plane normal vector of a circle from a parameter matrix when there are five markers in FIG. 2.

Figure 4:
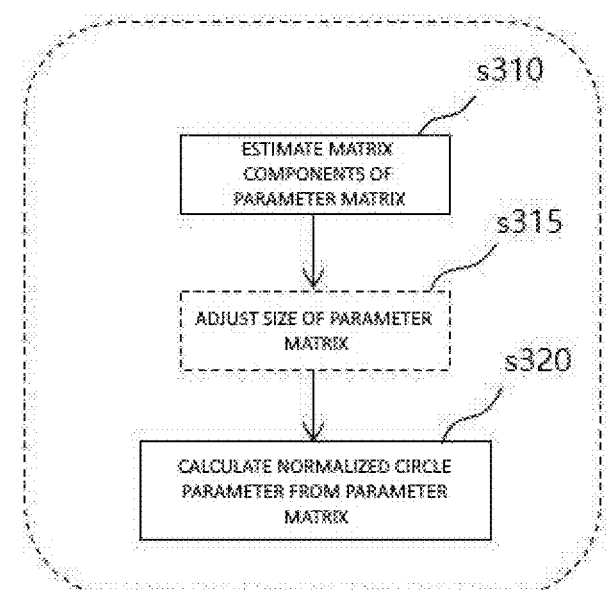
FIG. 4 is a flowchart illustrating operations of calculating normalized circle parameters including a center position, a radius, and a plane normal vector of a circle from a parameter matrix when there are five markers in FIG. 2.

Referring to FIG. 4, the operation s300b of calculating values of the center position, the radius, and the plane normal vector of the circle may include an operation s310 of defining the position values of the markers in the projected image and estimating matrix components respectively corresponding to the position values of the markers of the parameter matrix using a preset criterion, and an operation s320 of calculating normalized circle parameters including a normalized radius from the parameter matrix.

Next, referring again to FIG. 2, the method according to the present invention may further include the operation s400 of estimating the positions of the markers from the normalized circle parameters.

Detailed descriptions thereof are given as follows.

[Estimation of Parameter Matrix Q]

($a_i$, $b_i$) denotes the position of the $i^{th}$ marker in the projected image. Next, the following equation is applied for noise-free measuring of ($a_i$, $b_i$).

$$D_i^T q = 0 \quad \text{(Equation 5)}$$

Here, $$D_i = [a_i^2 \ 2a_i b_i \ b_i^2 \ 2a_i \ 2b_i \ 1]^T \in \mathbb{R}^6 \quad \text{(Equation 6)}$$

$$q = [q_{11} \ 2q_{12} \ q_{22} \ q_{13} \ q_{23} \ q_{33}]^T \in \mathbb{R}^6 \quad \text{(Equation 7)}$$

Here, $q_{ij}$ denotes an $\{i, j\}^{th}$ matrix component of the parameter matrix Q. Since the parameter matrix Q is a symmetric 3×3 matrix with six independent components, a vector q is a six-dimensional (6D) vector of the six independent components. When there is measurement noise at $(a_i, b_i)$, the vector q may be estimated using the following equation by applying least square minimization (s310).

$$\min_{q \in \mathbb{R}^6} q^T \left( \sum_i D_i D_i^T \right) q. \quad \text{(Equation 8)}$$

Since a scale of the parameter matrix Q is arbitrary, a meaningful solution may be obtained by deriving the following scale constraint.

$$q^T q = 1 \quad \text{(Equation 9)}$$

The least square minimization is an eigenvalue problem. Here, a solution of the vector q is an eigenvector of $$\sum_i D_i D_i^T$$

corresponding to the smallest eigenvalue. Finally, the parameter matrix Q is composed of components of the vector q.

Before entering the next operation, a size of the parameter matrix Q should be adjusted such that the second largest eigenvalue is 1 (s315). This operation may be performed by performing the following simple substitution.

$$Q \leftarrow Q/\lambda_{middle} \quad \text{(Equation 10)}$$

Here, $\lambda_{middle}$ denotes the second largest eigenvalue of the parameter matrix Q before the substitution. The reason for the above will be described in detail in the next section.

[Derivation of normalized circle parameter $(x_0, r, n)$ from parameter matrix Q]

Figure 5:
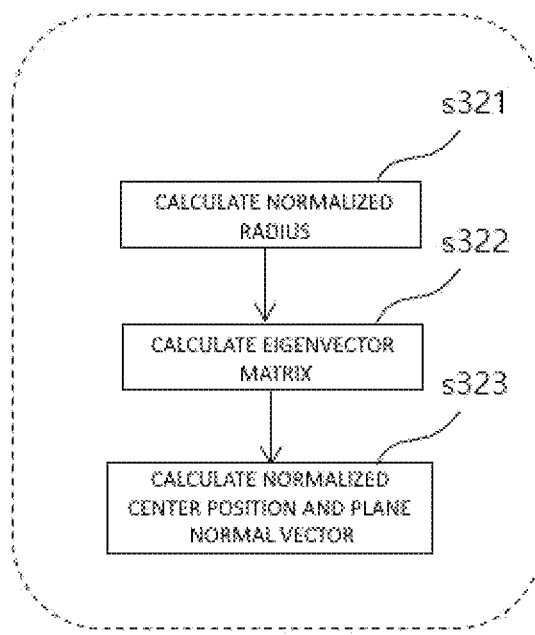
FIG. 5 is a flowchart illustrating operations of calculating the normalized circle parameter from the parameter matrix in FIG. 4.

FIG. 5 is a flowchart illustrating operations of calculating the normalized circle parameters from the parameter matrix in FIG. 4.

Referring to FIG. 5, the operation s320 of calculating the normalized circle parameters from the parameter matrix may include an operation s321 of calculating a normalized radius, an operation s322 of calculating an eigenvector matrix, and an operation s323 of calculating a normalized center position and plane normal vector.

Detained descriptions thereof are given as follows.

A method of calculating normalized circle parameters $(x_0, r, n)$ from an eigenvector and eigenvalue of the parameter matrix Q will be described. $v \in \mathbb{R}^3$ such as $v \perp x_0$ or $v \perp n$ is considered. The following equation is obtained by multiplying v by a right side of the above Equation 3.

$$Qv = v \quad \text{(Equation 11)}$$

Therefore, v denotes the eigenvector of the parameter matrix Q and the eigenvalue of the parameter matrix Q is $\lambda_3 = 1$ (here, the subscript "3" has a meaning indicated below). Other eigenvectors and eigenvalues are obtained by performing the following equation.

$$Q[x_0 n] = [x_0 n] S \quad \text{(Equation 12)}$$

Here, $$S = \begin{bmatrix} 0 & -1 \\ -r^2 & \|x_0\|^2 - r^2 \end{bmatrix} \in \mathbb{R}^{2 \times 2} \quad \text{(Equation 13)}$$

Since $n^T x_0 = 1$ by definition of $x_0$, the above equation is easily derived by multiplying $x_0$ and n by Equation 3. In Equation 12, an eigenvalue decomposition S is calculated by the following equation.

$$Q[x_0 \ n]X = [x_0 \ n]X \begin{bmatrix} \lambda_1 & 0 \\ 0 & \lambda_2 \end{bmatrix} \quad \text{(Equation 14)}$$

Here, a column of $X \in \mathbb{R}^{2 \times 2}$ denotes an eigenvector of S, and $\lambda_1$ and $\lambda_2$ denote corresponding eigenvalues. According to Equation 14, a column vector of $[x_0 \ n]X$ is the eigenvector of the parameter matrix Q, and corresponding eigenvalues are identical to the eigenvalue of S, that is, $\lambda_1$ and $\lambda_2$. That is, $\lambda_1$ and $\lambda_2$ denote roots of $\det(S - \lambda I) = 0$.

$$\lambda^2 - (\|x_0\|^2 - r^2)\lambda - r^2 = 0 \quad \text{(Equation 15)}$$

Next, since a product of $\lambda_1$ and $\lambda_2$ is $-r^2$, which is less than 0, one of two eigenvalues is positive and the other is negative. Further, when $\lambda = 1$ is substituted for the above equation, the left side becomes $1 - \|x_0\|^2$, which is 0 or negative by the Cauchy-Schwarz inequality at n and $x_o$. More specifically, since $\|n\|\|x_0\| = \|x_0\| \geq n^t x_0 = 1$, $1 - \|x_0\|^2 < 0$. Therefore, one eigenvalue is 1 or more and the other is negative, and, in summary, $\lambda_1 \geq 0$ and $\lambda_2 < 0$. The above results are important when describing the reason for scaling the size of the parameter matrix Q using Equation 10 in the future.

Since detQ is a product of all the eigenvalues, a normalized radius r is derived as follows (s321).

$$r = \sqrt{-\det Q} \quad \text{(Equation 16)}$$

$x_0$ and n are still unknown. In order to obtain $x_0$ and n, the fact that a diagonal trace of a matrix is the sum of all eigenvalues is used. Next, the following equation is applied (s322).

$$TrS = TrQ - 1 \quad \text{(Equation 17)}$$

By substituting Equations 13 and 16 for Equation 17, the following equation is obtained.

$$\|x_0\|^2 = TrQ - \det Q - 1 \quad \text{(Equation 18)}$$

By substituting Equations 16 and 18 for Equation 13, S may be completely identified and an eigenvector matrix X may be calculated.

The column of $[x_0 \ n]X$ is the eigenvector of the parameter matrix Q but the size of $[x_0 \ n]X$ is still unknown. $[x_0 \ n]X$ may be expressed by the following equation.

$$[x_0 n]X = [k_1 v_1 k_2 v_2] \quad \text{(Equation 19)}$$

Here, $v_1 \in \mathbb{R}^2$ and $v_2 \in \mathbb{R}^2$ are the eigenvectors of the parameter matrix Q corresponding to $\lambda_1$ and $\lambda_2$, respectively, and $k_1$ and $k_2$ are unknown sizes of the eigenvectors. Since $v_1$ and $v_2$ are eigenvectors of a symmetric matrix and are orthogonal to each other, the following equation may be obtained by multiplying a transpose of Equation 19 by itself $$X^T \begin{bmatrix} \|x_0\|^2 & 1 \\ 1 & 1 \end{bmatrix} X = X \begin{bmatrix} k_1^2 & 0 \\ 0 & k_2^2 \end{bmatrix} \quad \text{(Equation 20)}$$

Since a left side of Equation 20 is now all known, $k_1$ and $k_2$ are identified by the Equation 20. Next, the normalized center position $x_0$ and plane normal vector n may be easily calculated by inverting the eigenvector matrix X in Equation 19 (s323).

Since four solutions of $(k_1, k_2)$ may be obtained, four different $(x_0, n)$ (but still unique r) may be obtained. Considering that there are pairs of symmetric solutions $(x_0, n)$ and $(-x_0, -n)$, either of the pairs is unrealistic because it is in a direction opposite to the projection plane. When the solutions are eliminated, the number of solutions is reduced to two.

The development up to this point is valid only when the matrix Q is correctly scaled. Since $\lambda_1 > 0$, $\lambda_2 < 0$, and $\lambda_1 > 0$ and $\lambda_3 = 1$, the second largest eigenvalue should be 1. By determining whether the second largest eigenvalue is 1, the above fact may be verified. When it is determined that the second largest eigenvalue is not 1, the matrix Q should be adjusted by Equation 10.

[Estimation of $(X_0, R)$ and Marker Position]

Figure 6:
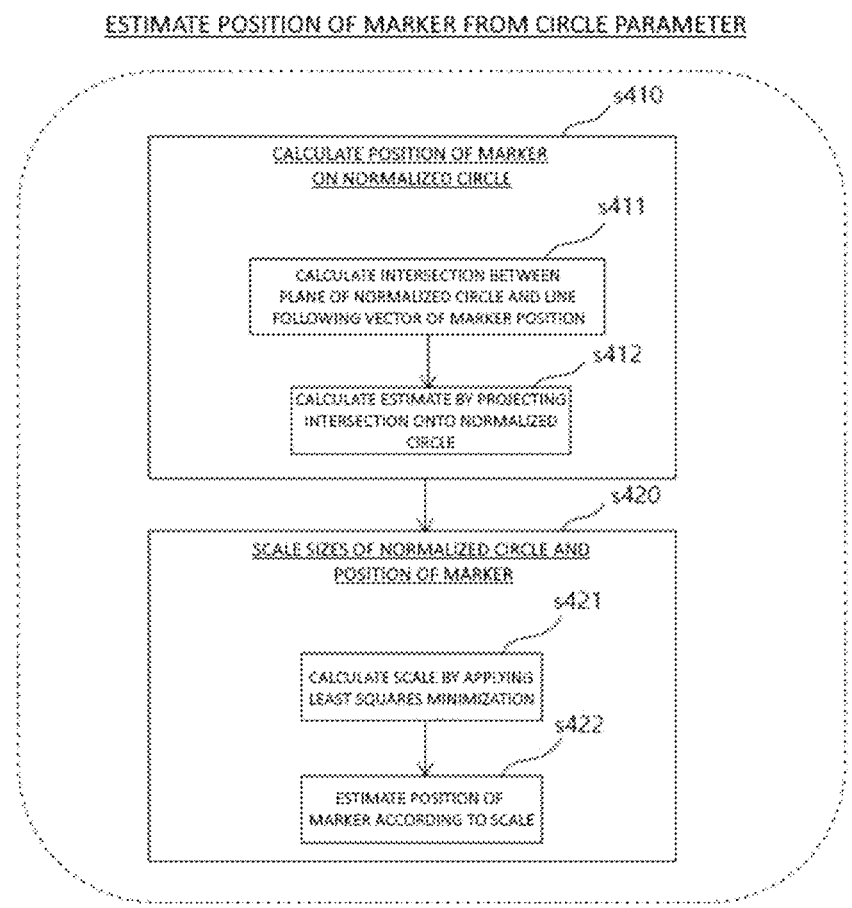
FIG. 6 is a flowchart illustrating operations of estimating a position of a marker from the normalized circle parameter in FIG. 2.

FIG. 6 is a flowchart illustrating operations of estimating the positions of the markers from the normalized circle parameters in FIG. 2.

Referring to FIG. 6, the operation s400 of estimating the positions of the markers from the normalized circle parameters may include an operation s410 of calculating the position of the marker on the normalized circle, and an operation s420 of scaling the sizes of the normalized circle and the position of the marker.

The operation s410 of calculating the position of the marker on the normalized circle may include an operation s411 of calculating an intersection between a plane of the normalized circle and a line following a vector of the marker positions (s411), and an operation s412 of calculating an estimate by projecting the intersection onto the normalized circle.

The operation s420 of scaling the sizes of the normalized circle and the position of the marker may include an operation s421 of calculating a scale by applying least squares minimization, and an operation s422 of estimating the position of the marker according to the scale.

Detailed descriptions thereof are given as follows.

The normalized circle parameters are calculated for the given parameter matrix Q, but the original circle parameters are still unknown. More accurately, the center position $X_0$ and the radius R of the marker are given from Equation 1 as follows.

$$X_0 = x_0 d, \quad R = rd \quad \text{(Equation 21)}$$

Here, d denotes an unknown scale. The scale d may be calculated using an actual marker distance of the interventional medical device. To this end, first, the position of the marker on the normalized circle may be calculated (s410), and then the sizes of the circle and the position of the marker may be scaled such that an actual marker distance matches a marker distance on the scaled circle (s420).

First, the position of the marker of the normalized circle is calculated. Considering the measurement error at $(a_i, b_i)$, the normalized circle has no point projected at exactly $(a_i, b_i)$. i) An intersection between the plane of the normalized circle and a line following a vector $(a_i, b_i, 1)$ may be calculated (s411), and then ii) a reasonable estimate may be obtained by projecting the intersection to the normalized circle (s412). The position of the $i^{th}$ marker on the normalized circle $x_i \in R^3$ is estimated as follows.

$$x_i = \frac{r}{\left\| \frac{1}{n^T p_i} p_i - x_0 \right\|} \left( \frac{1}{n^T p_i} p_i - x_0 \right) + x_0 \quad \text{(Equation 22)}$$

Here, $pi = [a_i, b_i, 1]$. $\delta \in R$ is defined as an arc length from x1 to xi along the normalized circle and a vector $\delta \in R$ which is a collection of the arc is defined as follows.

$$\delta = [\delta_{c,1} \delta_2 \ldots \delta_N]^T \in \mathbb{R}^N \quad \text{(Equation 23)}$$

When $l_i \in R$ is defined as an actual marker distance between a first marker and the $i^{th}$ marker and a vector $l = [l1\ l2\ \ldots\ ln] \in R$ is defined as a collection of the distance, the scale d may be obtained by applying the following minimization (s421).

$$\min_{d, l_0 \in R} \frac{1}{2} \left\| l + l_0 \vec{1} - d\delta \right\|^2 \quad \text{(Equation 24)}$$

Here, d denotes the scale, $l_0$ denotes an overall distance of movement of the marker, and $\vec{1} \in R^n$ denotes an n-dimensional work vector. A solution of the above minimization is as follows.

$$\begin{bmatrix} d \\ l_0 \end{bmatrix} = (L^T L)^{-1} L^T l \quad \text{(Equation 25)}$$

Here, $$L = [\delta \vec{1}] \in \mathbb{R}^{N \times 2} \quad \text{(Equation 26)}$$

Finally, the position of the marker may be estimated according to the scale.

The original circle parameters are obtained by substituting d for Equation 21, and the position of the $i^{th}$ marker is shifted by $l_0 + l_i$ along the circle with respect to x1d. There are two solutions of $(x_0, n)$ given in the above-described [Derivation of normalized circle parameter $(x_0, r, n)$ from parameter matrix Q]. A final solution may be obtained by selecting a solution having a small value of an objective function in Equation 24. However, the objective function is often not very discriminating particularly when the marker is far from the X-ray source. According to the present invention, since the two solutions are symmetric to each other with respect to a plane orthogonal to the z-axis, the clinician may easily identify the correct solution according to the anatomical structure of the surgical space.

In order to verify the feasibility and performance of the method according to the present invention, experiments were performed as follows. The purpose of the experiments is to verify accuracy of estimation of a 3D pose and curvature of a bendable interventional medical device using a single X-ray image.

[Experiment Setting]

Figure 7A:
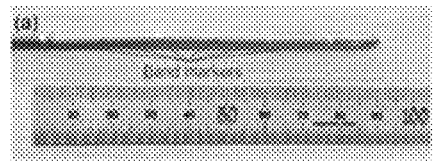
FIG. 7A is a view illustrating a cardiac catheter to which six band markers are attached.
Figure 7B:
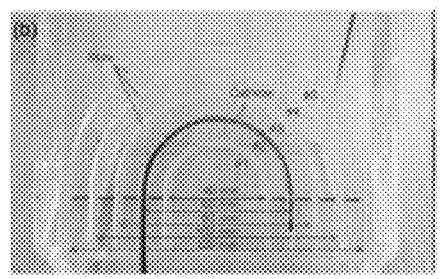
FIG. 7B is a view illustrating a catheter mount with five slots having different curvatures.
Figure 7C:
FIG. 7C is a view illustrating an X-ray scan of a cardiac catheter fixed to a mount.

FIG. 7A is a view illustrating a cardiac catheter to which six band markers are attached, FIG. 7B is a view illustrating a catheter mount with five slots having different curvatures, and FIG. 7C is a view illustrating an X-ray scan of a cardiac catheter fixed to a mount.

Referring to FIG. 7, a cardiac catheter (THERMO-COOL® SF Catheter, Biosense Webster Inc., CA, USA) was used for experiments. Six band markers made of a thin copper sheet were attached to a bendable portion of the catheter at a constant distance, as illustrated in FIG. 7A. An acrylic mount with five slots having different curvatures on an upper surface thereof was provided and used to fix the catheter at five known constant curvatures, as illustrated in FIG. 7B. The upper surface of the mount was designed to have an angle of 45° with respect to a lower surface of the mount. An X-ray image of the catheter fixed to the mount was obtained using a biplane X-ray device (XION-Artis, Siemens Healthneers, Erlangen, Germany), as illustrated in FIG. 7C. A distance between the band markers was about 15 mm. The distance was accurately measured using a digital caliper to obtain the vector 1.

[X-Ray Calibration]

Figure 8A:
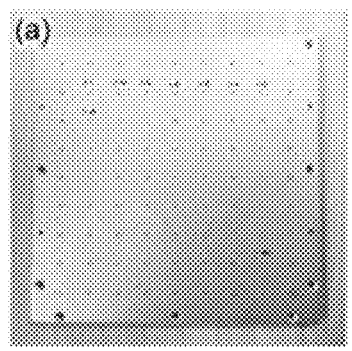
FIG. 8A is a view illustrating a two-dimensional (2D) calibration model.
Figure 8B:
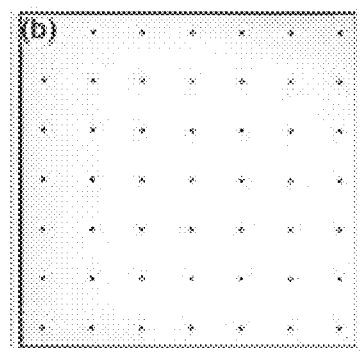
FIGS. 8B and 8C are views illustrating grid points automatically extracted from each of X-ray images for single X-ray calibration.
Figure 8C:
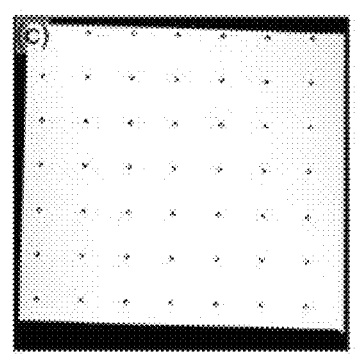
Figure 8D:
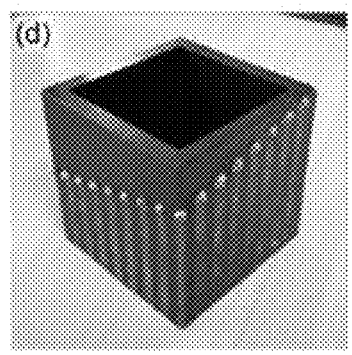
FIG. 8D is a view illustrating a three-dimensional (3D) calibration model.
Figure 8E:
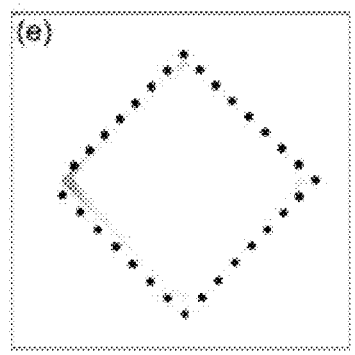
FIGS. 8E and 8F are views illustrating feature points automatically extracted from each of X-ray images for stereo X-ray correction.
Figure 8F:
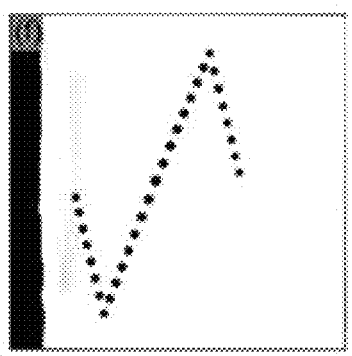

FIG. 8A is a view illustrating a two-dimensional (2D) calibration model, FIGS. 8B and 8C are views illustrating grid points automatically extracted from each of X-ray images for single X-ray calibration, FIG. 8D is a view illustrating a 3D calibration model, and FIGS. 8E and 8F are views illustrating feature points automatically extracted from each of X-ray images for stereo X-ray correction.

Referring to FIG. 8, in order to calibrate a biplane X-ray image, two different calibration models were prepared. A first model made of aluminum board was prepared as illustrated in FIG. 8A. On a surface of the model, 49 steel balls (ø2.0) were attached to corners of a 7×7 grid. A second model was made using a 3D printer and 31 steel balls (ø5.0) were attached to four side surfaces of the model at a constant distance (see FIG. 8D). The first calibration model was used for single X-ray calibration and the second calibration model was used for stereo X-ray calibration.

As a result of the calibration, internal and external parameters of each X-ray device were estimated. Based on the parameters, by performing stereo X-ray calibration, a 3D relationship between first and second X-ray source coordinates was estimated. A reprojection error of the stereo calibration was 1.7 pixels, and a resolution of the X-ray image was 1920×1920 pixels.

[Experiment Results]

Figure 9:
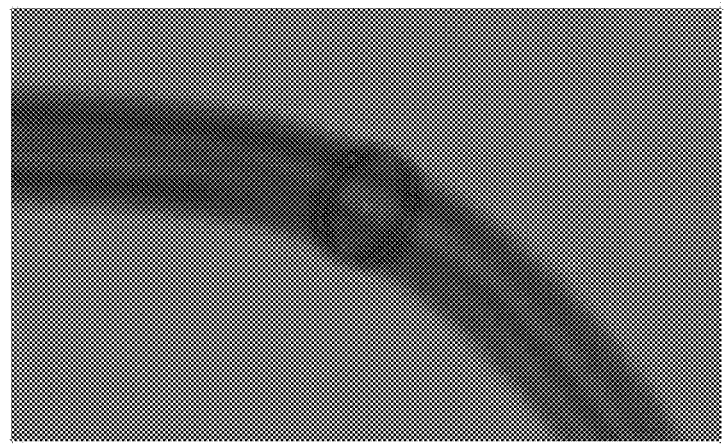
FIG. 9 is a view illustrating a method in which eight points are collected along each of markers and a center point obtained by fitting an arbitrary ellipse to the points is measured as a marker position in an X-ray image.
Figure 10A:
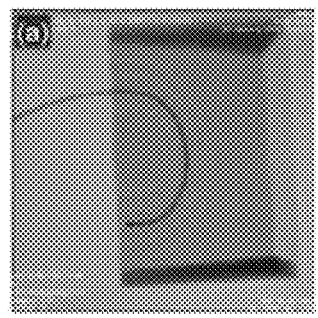
Figure 10B:
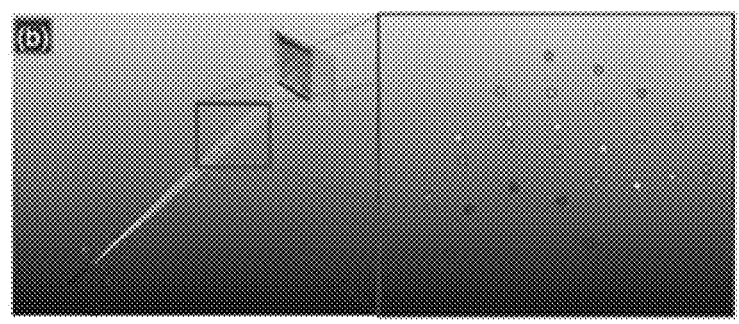

FIG. 9 is a view illustrating a method in which eight points are collected along each of markers and a center point obtained by fitting an arbitrary ellipse to the points is measured as a marker position in an X-ray image. FIG. 10 illustrates 3D reconstruction of a band marker position, FIG. 10A is a view illustrating an X-ray image #1, FIG. 10B is a view illustrating a marker position reconstructed by the method according to the embodiment of the present invention, FIG. 10C is a view illustrating an X-ray image #2, and FIG. 10D is a view illustrating a marker position reconstructed by a stereo triangulation method.

Referring to FIG. 9, five pairs of biplane X-ray images were obtained for the catheter mounted in the five slots of the catheter mount. The marker looks like an ellipse when being clearly imaged, and thus, in the present experiment, eight points were manually collected for each marker from the X-ray images to fit an ellipse and use $(a_i, b_i)$ as a center of the ellipse.

Referring to FIG. 10, when $(a_i, b_i)$ is collected for all X-ray images, 3D positions of the markers were calculated by triangulating the X-ray image pairs. The positions were used as actual data through experiments. Next, a method of estimating the 3D position of the marker using only one X-ray image from each pair of images was applied and the estimation results were compared with the actual data. The X-ray source of the images used in the method according to the embodiment of the present invention is about 700 mm from the catheter. As an embodiment of the present invention, only five markers disposed on the curved portion of each slot were used.

Figure 12A:
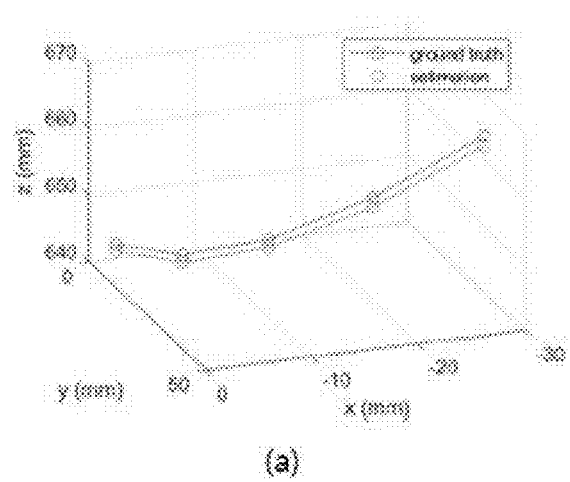
Figure 12B:
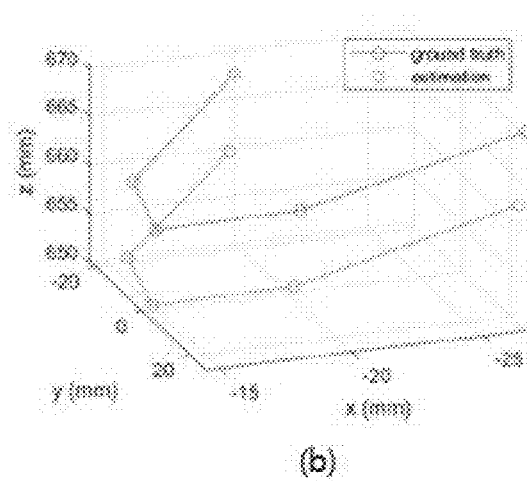
Figure 13:
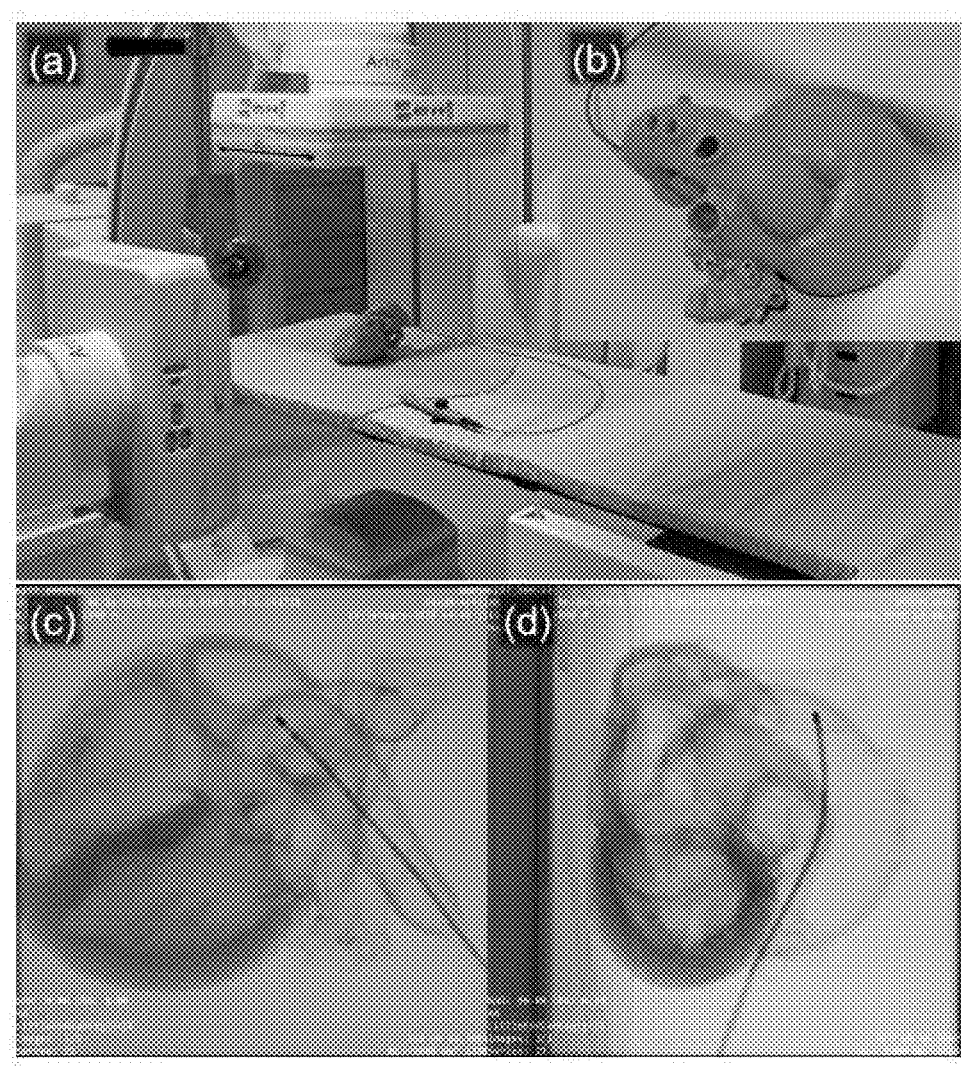
FIG. 13 illustrates views illustrating visibility test of band markers located in a heart phantom, wherein (a) is a view illustrating experimental setting, (b) is a view illustrating a heart phantom, (c) is a view illustrating an X-ray image (a posteroanterior (PA) view), and (d) is a view illustrating an X-ray image (a latero-lateral (LL) view).

FIG. 11 is a table showing errors in marker position, radius of curvature, and plane normal vector. FIG. 12 illustrates views illustrating comparison of estimated results and measured data, FIG. 12A is a view illustrating the best estimate, and FIG. 12B is a view illustrating the worst estimate. FIG. 13 illustrates views illustrating visibility test of band markers located in a heart phantom, FIG. 13A is a view illustrating experimental setting, FIG. 13B is a view illustrating a heart phantom, FIG. 13C is a view illustrating an X-ray image (a posteroanterior (PA) view), and FIG. 13D is a view illustrating an X-ray image (a latero-lateral (LL) view).

Referring to FIG. 11, the table of FIG. 11 shows errors for the positions of the markers, the radius of curvature, and the actual data of the plane normal vector of the method according to the present invention. Average/maximum errors of the positions of the markers, the radius of curvature, and the plane normal vector were 3.48 mm/7.86 mm, 0.59 mm/1.44 mm, and 0.77°/1.14°, respectively. Referring to FIG. 12, the best and worst estimates were presented.

Referring to FIG. 13, the catheter was inserted into a heart phantom (Normal Adult Model XC01T, CARDIO Simulator, crossMedical, Kyoto, Japan), and the visibility of the band marker attached to the catheter was confirmed in a posteroanterior (PA) view and a latero-lateral (LL) view.

In the present invention, a method of simultaneously estimating a 3D pose and a curvature of a bendable interventional medical device using only one X-ray image is disclosed. Accuracy of the method according to the present invention has been demonstrated to achieve average/maximum position errors of 3.48 mm/7.86 mm when being positioned about 700 mm from the X-ray source.

Since the accuracy should be further improved for clinic use, the following configuration may be additionally applied to the present invention to improve the accuracy in the future.

i) The markers need to be more sophisticated in terms of X-ray image clarity, and material selection and marker design may be included. ii) The current position of the marker are collected manually but the collection may also be automated to obtain positions more thoroughly and accurately. iii) An outline of the marker infers the distance and angle of the marker in relation to the X-ray source, but, for better estimation, information about the outline of the marker may be combined with an approaching method according to the present invention.

In addition, as a next operation to expand the scope of the present invention, the method according to the present invention may be generalized at a nonconstant curvature.

According to the present invention, it is possible to simultaneously estimate a 3D pose and a curvature of a bendable interventional medical device using only one X-ray image.

Further, according to the present invention, by providing 3D pose and curvature information of a bendable interventional medical device, such as a flexible catheter or a flexible endoscope, and helping clinicians make better decisions during surgery, it is possible for the clinicians to perform the surgery rapidly and to reduce radiation exposure of patient/medical staff.

The scope of the present invention is not limited to the description and expression of the embodiments explicitly described above. In addition, it is pointed out again that the scope of the present invention may not be limited by obvious changes or substitutions to those skilled in the art to which the present invention pertains.

What is claimed is:

1. A pose estimation method of an interventional medical device using a single-view X-ray image which is captured using a bendable interventional medical device equipped with a plurality of radiopaque markers and using an X-ray source, the pose estimation method comprising:
 an operation (a) of defining a circle assuming that the interventional medical device has a constant curvature;
 an operation (b) of extracting a position value of a marker from an X-ray image obtained by the X-ray source projecting X-rays onto the markers; and
 an operation (c) of setting a projection plane and estimating a shape of the circle using a position value of the marker extracted from a projected image obtained by perspective-projecting the circle onto the projection plane and using the position value of the marker extracted from the X-ray image;
 wherein, in the operation (c), when there are five radiopaque markers, the position value of the marker extracted from the projected image has parameters of a center position, a radius, and a plane normal vector of the circle; and
 wherein the operation (c) includes:
 an operation (c-1) of defining the position value of the marker extracted from the projected image using a parameter matrix and estimating each of matrix components corresponding to the position value of the marker in the parameter matrix using a preset criterion; and
 an operation (c-2) of calculating normalized circle parameters including a normalized radius, a normalized center position, and the plane normal vector from the parameter matrix.

2. The pose estimation method of claim 1, wherein, in the operation (c), when there are four radiopaque markers, the position value of the marker extracted from the projected image has parameters of a center position, a radius, and a rotation matrix of a circle.

3. The pose estimation method of claim 2, wherein the operation (c) includes an operation of calculating values of the parameters of the center position, the radius, and the rotation matrix of the circle by applying least squares minimization.

4. The pose estimation method of claim 1, further comprising, after the operation (c), an operation (d) of estimating the position of the marker from the normalized circle parameters.

5. The pose estimation method of claim 4, wherein the operation (d) includes:
 an operation of calculating a position of the marker on the normalized circle; and
 an operation of scaling sizes of the normalized circle and the position of the marker such that an actual marker distance matches a marker distance on the projected image.

6. The pose estimation method of claim 5, wherein the operation of calculating the position of the marker includes:
 an operation of calculating an intersection between a plane of the normalized circle and a line following a vector of marker positions on the projected image; and
 an operation of calculating an estimate by projecting the intersection onto the normalized circle.

7. The pose estimation method of claim 5, wherein the operation of scaling the normalized circle and the position of the marker includes:
 an operation of calculating a scale by applying least squares minimization using a length between the markers along the normalized circle and using an actual length between the markers; and
 an operation of estimating the position of the marker according to the scale.

8. The pose estimation method of claim 1, wherein, in the operation (c-1), the parameter matrix is a symmetric 3×3 matrix with six independent components.

9. The pose estimation method of claim 1, wherein, in the operation (c-1), the parameter matrix is estimated by applying least squares minimization.

10. The pose estimation method of claim 1, further comprising, after the operation (c-1) and before the operation (c-2), an operation of adjusting a size of the parameter matrix such that a second largest eigenvalue of the parameter matrix is 1.

11. The pose estimation method of claim 1, wherein the operation (c-2) includes an operation of calculating an eigenvector and a plurality of eigenvalues of the parameter matrix using a preset eigenvalue decomposition criterion and calculating a normalized radius.

12. The pose estimation method of claim 11, wherein, in the operation (c-2), the normalized circle parameters further include the normalized center position and the plane normal vector, and
 the operation (c-2) further includes:
 an operation of calculating an eigenvector matrix based on a trace of the parameter matrix being a sum of the eigenvalues of the parameter matrix; and
 an operation of identifying the eigenvalues of the parameter matrix based on the eigenvector of the parameter matrix being orthogonal to an eigenvector of a symmetric matrix and calculating the normalized center position and the plane normal vector by inverting the eigenvector matrix.

* * * * *